United States Patent [19]
Stewart et al.

[11] Patent Number: 4,614,594
[45] Date of Patent: Sep. 30, 1986

[54] BS AND W MEASUREMENT SYSTEM

[75] Inventors: Thomas L. Stewart, Houston; Florian C. Demny, Pasadena, both of Tex.

[73] Assignee: Shell Oil Company, Houston, Tex.

[21] Appl. No.: 773,681

[22] Filed: Sep. 9, 1985

[51] Int. Cl.⁴ .................. B01D 33/00; B01D 37/00
[52] U.S. Cl. .................. 210/746; 210/96.1; 210/138; 73/61.1 R
[58] Field of Search .................. 210/96.1, 138, 745, 210/746, 781; 73/61 R, 61.1 R; 324/61 R

[56] References Cited

U.S. PATENT DOCUMENTS

| 3,546,926 | 12/1970 | Dunavent, Jr. et al. | 73/61.1 R |
| 4,184,952 | 1/1980 | Stewart | 210/781 |
| 4,401,575 | 8/1983 | Stewart et al. | 210/746 |
| 4,492,639 | 1/1985 | Stewart et al. | 210/746 |
| 4,510,060 | 4/1985 | Stewart et al. | 210/746 |

Primary Examiner—Richard V. Fisher
Assistant Examiner—Linda S. Evans

[57] ABSTRACT

The basic water and sediment (BS&W) system compares a wet stream to a dry stream of the same oil in two electrical capacitance cells. A numerical zero offset is employed in the comparison to compensate for voltage output differences between the cells. The dry cell builds a small increase in its inherent offset from the wet cell because of its lower flow rate, which buildup is swept away when the wet fluid is run through both cells at a higher flow rate to determine the zero offset. To cancel the zero offset, the present invention alternates the flow to the two cells so that each cell experiences the same sequence of events alternately.

5 Claims, 1 Drawing Figure

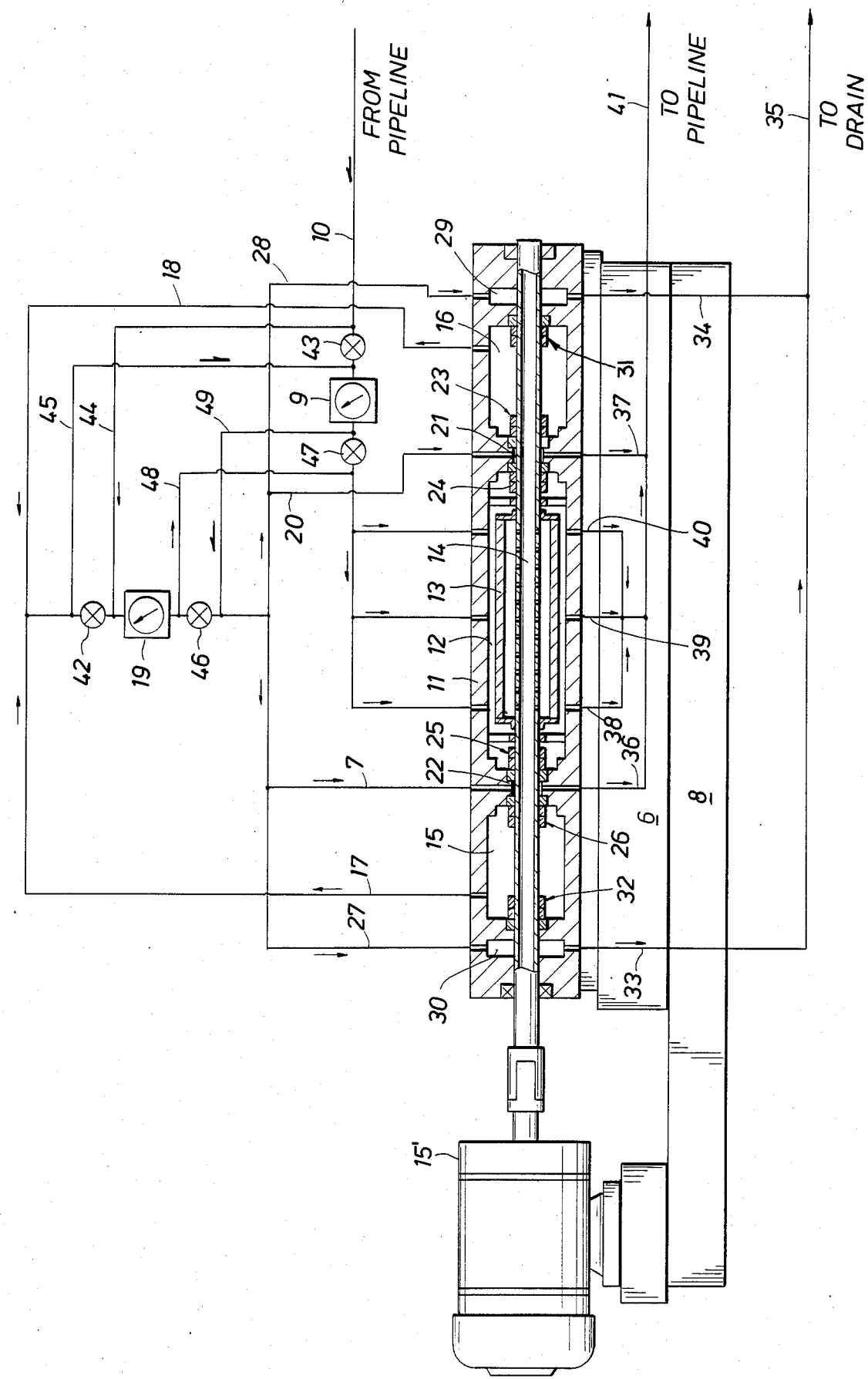

BS AND W MEASUREMENT SYSTEM

BACKGROUND OF THE INVENTION

A device for measurement of basic sediment and water (BS&W) in a predominantly non-aqueous stream (e.g. pipeline crude oil), is disclosed in U.S. Pat. No. 4,401,575. This device is an improvement on capacitance type instruments of the art which are dependent upon the extent to which the intrinsic dielectric constant of the subject varies with time. The gravity and physical composition of crude oil are two factors which determine its intrinsic dielectric constant. If one or both of these properties should vary, instruments measure the accompanying change in the dielectric constant as percent BS&W. This yields an inaccurate measurement of BS&W because instruments must be initially set to read zero BS&W as the intrinsic dielectric constant of the fluid. The capacitance type instruments of the prior art have no means for automatically correcting the zero BS&W setting to compensate for periodic variations in the oil properties mentioned. By comparison, the device of U.S. Pat. No. 4,401,575 provides for automatic compensation of BS&W measurements by producing a clean, dry sample of the line fluid for measurement of its intrinsic dielectric constant. In this way, the true BS&W content of the fluid is measured by finding the difference between the dielectric constants of the wet and dry streams.

The improvement over the prior art represented by the invention of U.S. Pat. No. 4,401,575 is substantial, and the present invention provides an additional improvement which even further increases the efficiency and accuracy of the invention of U.S. Pat. No. 4,401,575. Thus, it has been observed that the two capacitance cells of the BS&W instrument are identical, but not perfectly so, and therefore display a slight difference in voltage output when containing the same fluid. The cell testing and capacitance of a dry stream appears to build a small increase in its offset from the cell testing capacitance of a wet stream, due to the necessarily low flow rates through the dry stream capacitance cell, which buildup is swept away when the wet stream is run at a higher flow rate through both cells to determine zero offset (the "wet-wet" check). The magnitude of the offset is somewhat uncertain during the periods between wet-wet checks. Accordingly, it is desirable to cancel the zero offset with improved certainty and eliminate the wet-wet checks.

BRIEF DESCRIPTION OF THE DRAWINGS

The FIGURE schematically shows the flow paths of various streams within the apparatus of the invention.

SUMMARY OF THE INVENTION

The principal purpose of the present invention is to provide an improved BS&W measurement device and eliminate or reduce a tendency in the device to change zero offset between capacitance cells during operation.

Specifically, the present invention provides a process and apparatus for measuring the water and sediment content of a wet stream which is predominantly non-aqueous, comprising, removing a sample of the wet stream and measuring its capacitance in a first capacitance cell, feeding the wet stream sample into an outer chamber containing an inner chamber having a wall formed of a filter, rotating the inner chamber while pressuring the wet stream sample from the outer chamber into the inner chamber, withdrawing a clean dry stream sample from the inner chamber and measuring its capacitance in a second capacitance cell, and periodically passing the wet stream sample to the second capacitance cell and the dry stream sample to the first capacitance cell.

DESCRIPTION OF THE PREFERRED EMBODIMENTS

In accordance with the present invention, a process and apparatus are provided for incorporating the water/oil emulsion separator in U.S. Pat. No. 4,401,575 into a complete system for determining basic sediment and water in crude oil, other hydrocarbons, or other substantially non-aqueous systems. This invention is particularly concerned with a slight difference in voltage output within the two electrical capacitance cells of the system when containing the same fluid. The dry cell (containing a dry stream sample) appears to build a small increase in its offset from the wet cell (containing a wet stream sample) due to its necessarily low flow rate, which buildup is swept away when the wet stream is run at a higher flow rate through both cells to determine the zero offset (the "wet-wet" check). The magnitude of the offset is somewhat uncertain during the period between wet-wet checks. Accordingly, the present invention alternates the flow to the two cells so that each cell experiences the same sequence of events alternately. Preferably, at least about half the time the first cell will experience a high flow rate of the wet stream while the second cell experiences a low flow rate of the dry stream. At least about the remaining half of the time the second cell preferably experiences a high flow rate of the wet stream while the first cell experiences a low flow rate of the dry stream. The zero offset will cancel when an even number of these alternations is averaged as to water content measurement.

A sectional view of the present invention is provided in the FIGURE with the flow streams shown schematically. Crude oil or other fluid containing a small amount of water is taken from a pipeline or other storage or transport via line 10 and passed through a wet stream capacitance measurement cells 9, and then through a housing 11 supported by structures 6 and 8, and then into wet stream chamber 12. Cell 9 determines the capacitance of the wet stream. From chamber 12, the wet stream is forced through filter 13 and into hollow drive shaft 14. Hollow drive shaft 14 and filter 13 are spun by a motor or other drive means 15'. While the present invention is not limited to the following theory, it appears that the resulting centrifugal force substantially prevents the water and sediment capable of otherwise passing through filter 13, from entering hollow shaft 14, and any water or sediment that may enter shaft 14 is forced outwardly back into chamber 12. Dry fluid in hollow shaft 14 passes outwardly into dry stream chambers 15 and 16. Dry stream from chambers 15 and 16 then is passed via lines 17 and 18 through a dry stream capacitance measurement cell 19 which determines the capacitance of the dry stream. As above noted, comparisons of the capacitances of the dry stream with the capacitance of the wet stream facilitates determining true BS&W content of the wet stream.

A portion or all of the dry stream from cell 19 is passed via lines 7 and 20 into spaces 21 and 22 separating seals 23 and 24 and seals 25 and 26, respectively, which separate wet stream chamber 12 from dry stream chambers 15 and 16. An additional minor portion of the dry sample stream may be passed via lines 27 and 28 into spaces 29 and 30, which separate outer seals 31 and 32 from the atmosphere. Spaces 29 and 30 are at atmospheric pressure, and accordingly, the dry stream therefrom is passed via lines 33, 34 and 35 to drain or disposal. Dry stream from spaces 21 and 22 is passed via lines 36 and 37 along with wet stream from lines 38, 39 and 40 back to the pipeline or other storage or transport via line 41.

To divert stream 10 to cell 19, valves 42 and 43 are closed whereby fluid passes through line 44 and into cell 19. Streams 17 and 18 then pass through line 45 and into cell 9. Valves 46 and 47 are also closed so that stream 48 passes into line 10 downstream of valve 47 and stream 49 passes into the line downstream of valve 46. This effectively alternates the flow between the two capacitance cells 9 and 19. Control means (not shown) well known to those skilled in the art may be provided to control the times of opening and closing valves 46 and 47.

While the present invention has been described principally in connection with the basic sediment and water instrument and in terms of crude oil and wet and dry streams of said crude oil, it will be apparent that the basic principles of the invention are adaptable to other processes and apparatus utilizing non-oil streams.

What is claimed is:

1. A process for measuring the water and sediment content of a wet stream which is predominantly non-aqueous, comprising:
    removing a sample of the wet stream and measuring its capacitance in a first capacitance cell;
    feeding the wet stream sample into an outer chamber containing an inner chamber having a wall formed of a filter;
    rotating the inner chamber while pressuring the wet stream sample from the outer chamber into the inner chamber;
    withdrawing a clean dry stream sample from the inner chamber and measuring its capacitance in a second capacitance cell; and
    periodically passing the wet stream sample to the second capacitance cell and the dry stream sample to the first capacitance cell.

2. The process of claim 1 including comparing the capacitance of the wet stream sample with the capacitance of the clean dry stream sample to facilitate determining the basic sediment and water content of the wet stream.

3. The process of claim 1 wherein the wet stream sample is pipeline crude oil.

4. An apparatus for measuring the water and sediment content of a wet stream which is predominantly non-aqueous, comprising:
    means for removing a sample of the wet stream and measuring its capacitance in a first capacitance cell;
    means for feeding the wet stream sample into an outer chamber containing an inner chamber having a wall formed of a filter;
    means for rotating the inner chamber while pressuring the wet stream sample from the outer chamber into the inner chamber;
    means for withdrawing a clean dry stream sample from the inner chamber and measuring its capacitance in a second capacitance cell; and
    means for periodically passing the wet stream sample to the second capacitance cell and the dry stream sample to the first capacitance cell.

5. The apparatus of claim 4 including means for comparing the capacitance of the wet stream sample with the capacitance of the clean dry stream sample to facilitate determining the basic sediment and water content of the wet stream.

* * * * *